(12) United States Patent
Schwartz et al.

(10) Patent No.: US 11,324,713 B2
(45) Date of Patent: *May 10, 2022

(54) ORGANOARSENIC COMPOUNDS AND METHODS FOR THE TREATMENT OF CANCER

(71) Applicant: SOLASIA PHARMA K.K., Tokyo (JP)

(72) Inventors: Brian Eric Schwartz, Woodbridge, CT (US); Jonathan Lewis, Fairfield, CT (US); Philip B. Komarnitsky, Chestnut Hill, MA (US)

(73) Assignee: SOLASIA PHARMA K.K., Tokyo (JP)

( * ) Notice: Subject to any disclaimer, the term of this patent is extended or adjusted under 35 U.S.C. 154(b) by 79 days.

This patent is subject to a terminal disclaimer.

(21) Appl. No.: 17/071,435

(22) Filed: Oct. 15, 2020

(65) Prior Publication Data

US 2021/0038556 A1    Feb. 11, 2021

Related U.S. Application Data

(63) Continuation of application No. 14/524,586, filed on Oct. 27, 2014, now Pat. No. 10,842,769, which is a continuation of application No. 13/059,176, filed as application No. PCT/US2009/053858 on Aug. 14, 2009, now abandoned.

(60) Provisional application No. 61/189,511, filed on Aug. 20, 2008.

(51) Int. Cl.
| | | |
|---|---|---|
| *A61K 31/285* | (2006.01) | |
| *A61K 31/455* | (2006.01) | |
| *A61K 31/60* | (2006.01) | |
| *A61P 35/00* | (2006.01) | |
| *A61P 35/02* | (2006.01) | |
| *A61K 9/00* | (2006.01) | |

(52) U.S. Cl.
CPC .......... *A61K 31/285* (2013.01); *A61K 9/0019* (2013.01); *A61K 31/455* (2013.01); *A61K 31/60* (2013.01); *A61P 35/00* (2018.01); *A61P 35/02* (2018.01)

(58) Field of Classification Search
CPC .... A61K 31/285; A61K 31/455; A61K 31/60; A61P 35/00; A61P 35/02
See application file for complete search history.

(56) References Cited

U.S. PATENT DOCUMENTS

| | | |
|---|---|---|
| 234,972 A | 5/1944 | Hopkinson et al. |
| 6,191,123 B1 | 2/2001 | Uckun et al. |
| 6,482,815 B1 | 11/2002 | Uckun et al. |
| 6,482,816 B1 | 11/2002 | Uckun et al. |
| 6,911,471 B2 | 6/2005 | Zingaro et al. |
| 6,995,188 B2 | 2/2006 | Zingaro et al. |
| 7,405,314 B2 | 7/2008 | Zingaro et al. |
| 761,900 A1 | 11/2009 | Zingaro et al. |
| 2002/0013371 A1 | 1/2002 | Warrell et al. |
| 2002/0183385 A1 | 12/2002 | Ellison et al. |
| 2003/0176359 A1 | 9/2003 | Neuwelt et al. |
| 2004/0028750 A1 | 2/2004 | Lu |
| 2004/0034095 A1 | 2/2004 | Zingaro et al. |
| 2006/0128682 A1 | 6/2006 | Zingaro et al. |
| 2007/0183972 A1 | 8/2007 | Gutsch et al. |
| 2008/0139629 A1 | 6/2008 | Wallner et al. |
| 2009/0047243 A1 | 2/2009 | Rickles et al. |
| 2009/0053168 A1 | 2/2009 | Rickles et al. |

FOREIGN PATENT DOCUMENTS

| | | |
|---|---|---|
| CN | 101076533 | 11/2007 |
| EP | 1002537 A1 | 5/2000 |
| JP | 2005-527487 A | 9/2005 |
| JP | 2008-506710 | 3/2008 |
| SU | 188971 A | 11/1966 |
| WO | WO 199924029 A1 | 5/1999 |
| WO | WO 0305701 A2 | 7/2003 |
| WO | WO 2006020048 A2 | 2/2006 |

(Continued)

OTHER PUBLICATIONS

Sakurai et al."Toxicity of a trivalent organic arsenic compound, dimethylarsinous glutathione in a rat liver cell line (TRL 1215)" British Journal of Pharmacology (2006) vol. 149 pp. 888-897.

Schoene et al. "Specification of arsenic-containing chemical warfare agents by gas chromatographic analysis after derivatization with thioglcoli acid methyl ester" Journal of Chromatography (1992) vol. 605, No. 2, pp. 257 262.

Scott et al. Reactions of arsenic (III) and arsenic (V) species with glutathione Chemical Research in Toxicology (1993) vol. 5, No. 1, pp. 102-106.

Soignet et al. "Clinical study of an organic arsenic melarsophrol, in patients with advance leukemia" Cancer Chermother. Pharmacol. (1999) vol. 44, pp. 417-421.

Soignet et al. "Dose-ranging and clinical pharmacologic study of arsenic trioxide in patients with advanced hermatologic cancers" Blood (1999) vol. 94, pp. 1247a.

(Continued)

*Primary Examiner* — Savitha M Rao
(74) *Attorney, Agent, or Firm* — Leason Ellis LLP

(57) ABSTRACT

A method for treating a lymphoma selected from non-Hodgkin's and Hodgkin's lymphoma comprising administering an organoarsenic compound having a structure of the formula (I) wherein X is S or Se and $R_1$ and $R_2$ are independently $C_{1-30}$alkyl ($R_3$, $R_{3'}$, $R_4$, $R_5$, W and "n" are as defined in claim 1) in particular where the compound is S-dimethylarsinoglutathione, N-(2-S-dimethylarsinothiopropionyl)glycine, 2-amino-3-(dimethylarsino)thio-3-methylbutanoic acid, S-dimethylarsino-thiosuccinic acid or S-dipropylarsino-1-thioglycerol.

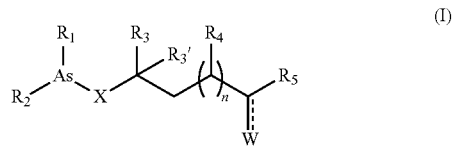

2 Claims, No Drawings

(56) References Cited

FOREIGN PATENT DOCUMENTS

| WO | WO 2007/027344 | 3/2007 |
|---|---|---|
| WO | WO 2007027344 A2 | 3/2007 |
| WO | WO 2007082104 A2 | 7/2007 |
| WO | WO 2008054594 A2 | 5/2008 |
| WO | WO 2009011893 A2 | 1/2009 |
| WO | WO 2009011897 A1 | 1/2009 |
| WO | WO 2009151569 A2 | 12/2009 |

OTHER PUBLICATIONS

Styblo et al "Comparative inhibition of yeast glutathione reductase by arsenicals and arsenothiols" Chemical Research in Toxicology (1997) vol. 10, No. 1, pp. 27-33.
Tallman "Therapy of acute promyelocytic leukemia: all tans retinoic acid and beyond" Leukemia (1998) vol. 12 (Supplemental Content), No. 1, pp. 837 840.
Tsalev et al. "Flow injection hydride generation atomic absorption spectometric study of the automated on line pre reduction of arsenate, methylarsonate and dimethylarsinate and high-performance liquid chromatographic separation of their l-cysteine complexes" Talanta (2000) vol. 51, No. 6, pp. 1059-1068.
Tsao et al. "Optically Detected Magnetic Resonance Study of the Interaction of Arsenic (III) Derivative of Cacodylic Acid with EcoRI Methyl Transferase" Biochemistry(1991) vol. 30, No. 18, pp. 4565-4572.
Vega et al. "Differential effects of trivalent and pentavelent arsenicals on cell proliferation and cytokine secretion in normal human epiderman keratinocytes" Toxicology and Applied Pharmacology (2001) vol. 172, No. 3, pp. 225-232.
West "Solid State Chemistry and Its Applications" (1988) pp. 358 and 365.
Wiernik et al. "Phase 1 trial of arsenic trioxide (As2O3) in patients with relapsed/refractory acute myeloid leukemia, blast crisis of CML or myelodysplasia" Blood (1999) vol. 94. pp 2283a.
Zhang et al. "Arsenic trioxide treated 72 cases of acute promyelocytic leukemia" Chin. J. Hematol. (1996) vol. 17, pp. 58-62.
Zingaro "Seleno and Thio Sugar Esters of Group VA Acids" Chemica Scripta (1975) vol. BA, pp. 51-57.
Zingaro et al. "Thio and Seleno Sugar Esters of Dialkylarsinous Acids" Carbohydrate Research (1973) vol. 29, pp. 147-152.
American Conference of Governmental Industrial Hygienists, Inc. (ACGIH). Arsenic and soluble compounds, including arsine. Documentation of the Threshold Limit Values and Biological Exposure Indices, sixth edition, 1991.
Aslandis et al. "Methylarsino-substituted hydroxy carboxylate ester" Chemiker-Zeitung(1988) vol. 112, No. 4, pp. 125-127.
Bachleitner Hofmann et al. "Arsenic trioxide and ascorbic acid: synergy with potent |β implications for the treatment of acute myeloid leukemia" British Journal of Haematology (2001) vol. 112, No. 3, pp. 783-786.
Banks et al. "Biomolecules Bearing the S- or SeAsMe2 Function: Amino Acid and Steroid Derivatives" Journal of Medicinal Chemistry (1979) vol. 22, No. 5, pp. 572-575.
Barber "Hydrolysis of arylthioarsinites Hydrolysis of arylthiorsinites" Journal of the Chemical Society (1932) Abstracts 1365-9.
Beckermann "Determination of monovethylarsonic acid and dimethylarsinic acid by derivatization with thioglycolic acid methyl ester and gas liquid chromatographic separation" AnalyticaChimica Acta (1982) vol. 135, No. 1, pp. 77-84.
Beliles "The Metals" Patty's Industrial Hygiene and Toxicology, Fourth Edition (1994) pp. 1913-1925.
Caira "Crystalline Polymorphism of Organic Compounds" Topics in Current Chemistry (1998) vol. 198. pp 163-208.
Calleja et al. "Differentiating agents in pediatric malignancies: all trans retinoic acid and arsenic in acute promyelocytic leukemia" Current Oncology Reports (2000) vol. 2. pp. 519-523.
Chen et al. "6-thio-and-seleno alpha D glucose esters of dimethylarsinous acid" Carbohydrate Research (1976) vol. 50, pp. 53-62.
Chen et al. "Methylated Metabolites of Arsenic Trioxide Are More Potent Than Arsenic Trioxide as Apoptotic but not Differentiation Inducers in Leukemia and Lymphoma Cells" Cancer Research (2003) vol. 63, pp. 1853-1859.
Chen et al. "Synthesis of 1 and 6 S and 1 and 6 Se derivatives of 2-amino-2-deoxy-alpha/beta-D-glucopyrasone" J. Chemical Soc., Perkins Trans. (1980) vol. 1, pp. 2287-2293.
Cheson, "New drug development in non-hodgkin lymphoma" Current Oncology Reports (2001) vol. 3, pp. 250-259.
Craig et al. "Phase II trial of darniaparsin (ZIO-101) in leukemias and lymphomas" 99th AACR Annual Meeting (2008) Abstract.
Cullen et al. "The metabolism of methylarsine oxide and sulfide" Applied Organometallic Chemistry (1989) vol. 3, No. 1, pp. 71-78.
Cullen et al. "The reaction of methylarsenicals with thiols: some biological implications" Journal of Inorganic Biochemistry (1984) vol. 21, No. 3, pp. 179-194.
Cuzick et al. "Medicinal arsenic and internal malignancies" Br. J. Cancer (1982) vol. 45, pp. 904-911.
Daniel et al. "Dimethylarsinous Acid Esters of 1-Tio-and-Seleno galactose, A New Class of Potential Carcinostatic Agents" Phosphorus and Sulfur (1978) vol. 4, pp. 179-185.
Emran et al. "Synthesis and biodistribution of raarsenic labeled dimethylarsinothiols: derivatives of pennicillamine and mercaptoethanol" International Journal of Nuclear Medicine and Biology (1984) vol. 11, No. 3 4, pp. 259-261.
European Search Report and Written Opinion for European Application No. 09808635.8 dated Sep. 2, 2011.
Fatouros et al. "Preparation and properties of arsonolipid containing liposomes" Chemistry and Physics of Lipids (2001) vol. 109, pp. 75-89.
Forkner et al. "Arsenic as a therapeutic agent in chronic myeloid leukemia" JAMA (1931) vol. 97, No. 1, pp. 3-6.
Gao etal "Synthesis of S-dialkylarsino-3-mercapto-1,2 propanediols and evaluation of their anticancer activity" Biooganic & Medicinal Chemistry (2007) vol. 15, pp. 2660-2666.
Geissler et al. "In vivo effects of arsenic trioxide in refractory acute myeloid leukemia other than acute promyelocytic leukemia" Blood (1999) vol. 94 pp. 4230a.
Gillard et al. "Amylo 1,6 glucosidase/4 alpha glucanotransferase" The Journal of Biological Chemistry (1980) vol. 255, No. 18, pp. 8451-8457.
Goyer et al. "Toxic effects of metals" Casarett and Doull's Toxicology: The Basic Science of Poisons, Fifth Edition (1996) pp. 691-698.
Grignani et al. "The acute promyelocytic leukemia specific PML-RAR alpha fusion protein inhibits differentiation and promotes survival of myeloid precursor cells" Cell (1993) vol. 74, pp. 423-431.
Hirano et al. "Cytotoxic effects of S-(dimethylarsino)-glutathione:a putative intermediate metabolite of inorganic arsenicals" Toxicology (2006) vol. 227, No. 1 2, pp. 45-52.
Hu et al. "Arsenic in cancer therapy" Anti-Cancer Drugs (2005) vol. 16, No. 2, pp. 119-127.
Huang et al. "Internal Diseases Diagnosis and Differential Diagnostics—Section 8: Lymphoma" Hubei Science and Technology Press (2001) pp. 1090-1093.
Hughes et al. "Dose dependent effects on the disposition of monomethylarsonic acid and dimethylarsinic acid in the mouse after intravenous administration" Journal of Toxicol. Environ. Health (1998) vol. 53, No. 2, pp. 95-112.
IARC "Some metals and metallic compounds" IARC Monographs on the Evaluation of the Carcinogenic Risk of Chemicals to Man (1980) vol. 23, pp. 39-141.
International Search Report and Written Opinion for International Applicational No. PCT/US2009/053858 dated Nov. 4, 2009.
Ionov et al. "Reaction to tertiary arsine sulfides with alkyl chlorocarbonates" Zhurnal Obshchei Khimii (1976) vol. 46, No. 11, pp. 2555-2558.
Kala et al. "The MRP2/cMOAT transporter and arsenic glutathione complex formation are required for biliary excretion of arsenic" J. Biol. Chem. (2000) vol. 275, No. 43, pp. 33404-33408.

(56) References Cited

OTHER PUBLICATIONS

King et al. "Relation between the constitution of arsenicals and their action on cell division" Journal of the Chemical Society Abstracts (1950) pp. 2086-2088.
Kitamura et al. "New retinoids and arsenic compounds for the treatment of refractory acute promyelocytic leukemia clinical and basic studies for the next generation" Cancer Chemother. Pharmacol. (1997) vol. 40 (Supplemental Content), pp. S36-S41.
Knock et al, "The use of selected sulfhydryl inhibitors in a preferential drug attack on cancer" Surg. Gynecol. Obstet. (1971) vol. 133, pp. 458-466.
Kober et al. "Reaction of (dimethylamino) dimethylarsine with 1, 2 diols" Zeitschrift Fuer Anorganisce Und Allegemeine Chemie (1974) vol. 406, No. 1, pp. 52-61.
Konig etal. "Comparative activity of melarsoprol and arsenic trioxide in chronic B-cell leukemia lines" Blood (1997) vol. 90, pp. 562-570.
Lallemand Breitenbach et al. "Retinoic acid and arsenic synergize to eradicate leukemic cells in a mouse model of acute promyelocytic leukemia" Journal of Experimental Medicine (1999) vol. 189. pp 1043-1052.
Lam et al. "Spectroscopic studies of arsenic (III) binding to *Escherichia coli* RI methyltransferase and to two mutants, C223S and W183F" Biochemistry (1992) vol. 31, No. 43, pp. 10438-10442.
Lin et al. "Methylarsenicals and arsinothiols are potent inhibitors of mouse liver thioredoxin reductase" Chemical Research in Toxicology (1999) vol. 12, No. 10, pp. 924-930.
Mandic et al. Tumor angiogenesis and endometrial cancer Archive of Oncology (2002) vol. 10, No. 2, pp. 79-81.
Mester et al. "Specification of dimethylarsinic acid and monomethylarsonic acid by gas chromatography mass spectrometry" Journal of Chromatography (1999) vol. 832, No. 1 2, pp. 183-190.
Mountain et al. "Chemotherapy Studies in an Animal Tumor Spectrum: III. Evaluation of the Toxicity Differentil Index" Cancer Research (1966) vol. 26, pp. 258-2644.
Quintas-Cardama et al. "Chemical and Clinical Development of Darinaparsin, a Novel Organic Arsenic Derivative" Anti-Cancer Agents in Medicinal Chemistry (2008) vol. 8, No. 8, pp. 904-909.
Raab et al. "Arsenic-glutathione compleses—their stability in solution and during separation by different HPLC modes" J. Anal. Al. Spectrom. (2004) vol. 19, No. 1, pp. 183-190.
Rivi et al. "Organic arsenical melarsoprol shows growth suppressive activity via programmedcell death on myeliod and lymphoid leukemia derived cell lines" Blood (1996) vol. 88 (Supplemental Content), pp. 68a.
Rosenthal et al. "The Synthesis and Characterization of Thio Sugar Esters of Diorganylarsinous Acids" Phosphorus and Sulfur (1980) vol. 9 ,pp. 107-116.
Rousselot et al. "Use of arsenic trioxide (As2O3) in the treatment of chronic myelogenous leukemia: In vitro and in vivo studies" Blood (1999) vol. 94 pp. 4457a.
Truong et al. "Optimal design methodologies for configuration of supply chains" International Journal of Production Research (2005) vol. 43, No. 11, pp. 2217-2236.
Rudiger et al. Peripheral T-cell lymphoma (excluding anaplastic large-cell lymphoma): results from the non-Hodgkin's lymphoma classification project. Annals of Oncology, 13: 140-149, 2002.
Brincker et al. Non-hodgkin's lymphoma subtypes over time in an unselected population fo 646 patients: a study of clinic-pathological data and incidence based on a review using the REAL-classification. Leukemia & Lymphoma. vol. 3905-60, pp. 531-541, 2000.
Hanahan et al. Hallmarks of Cancer: The Next Generation, Cell, 141 (5), pp. 646-674.
Rudiger et al. (Annals of Oncology, 13: 140-149, 2002).
Office Action dated Jan. 20, 2014 for the corresponding European Patent Application No. 09808635.8.
Office Action dated May 5, 2015 for the corresponding European Patent Application No. 09808635.8.
Office Action dated Jul. 4, 2016 for the corresponding European Patent Application No. 09808635.8.
Office Action dated Aug. 29, 2017 for the corresponding European Patent Application No. 09808635.8.
European Search Report dated Jun. 27, 2018 for the related European Patent Application No. 18174817.9.
Office Action dated May 21, 2013 for the corresponding Chinese Patent Application No. 200980135654.2.
Office Action dated Oct. 9, 2016 for the corresponding Chinese Patent Application No. 201410740427.5.
Office Action dated Oct. 20, 2015 for the corresponding Korean Patent Application No. 10-2011-7006250.
Office Action dated Oct. 20, 2016 for the corresponding Korean Patent Application No. 10-2011-7006250.
Written Opinion dated Jul. 19, 2012 for the corresponding Singaporean Patent Application No. 201101186-3.
Written Opinion dated Jun. 19, 2013 for the corresponding Singaporean Patent Application No. 201101186-3.
Examination Report dated Apr. 9, 2014 for the corresponding Singaporean Patent Application No. 201101186-3.
Office Action dated Dec. 10, 2013 for the corresponding Japanese Patent Application No. 2011-523888.
Office Action dated Jan. 28, 2016 for the corresponding Japanese Patent Application No. 2014-108079.
Office Action dated Sep. 28, 2017 for the corresponding Japanese Patent Application No. 2016-191062.
"Guidance for Industry Estimating the Maximum Safe Starting Dose in Initial Clinical Trials for Therapeutics in Adult Healthy Volunteers", *Center for Drug Evaluation and Research (CDER), U.S. Department of Health and Human Services Food and Drug Administration*, Jul. 2005 http://www.fda.gov/downloads/Drugs/Guidances/UCM078932.
Coiffier et al., Results from a Pivotal, Open-Label, Phase II Study of Romidepsin in Relapsed or Refractory Peripheral T-Cell Lymphoma After Prior Systemic Therapy, Journal of Clinical Oncology, 2012, 30:631-636.
O'Connor et al., Pralatrexate in Patients with Relapsed or Refractory Peripheral T-Cell Lymphoma: Results from the Pivotal PROPEL Study, Journal of Clinical Oncology, 2011, 29:1182-1189.
Hosein et al., A multicenter phase II study of darinaparsin in relapsed or refractory Hodgkin's and non-Hodgkin's lymphoma, American Journal of Hematology, 2011, 87: 111-114.
Wikipedia, Body surface area, 4 pages.
Broccoli et al., Peripheral T-cell lymphoma, not otherwise specified, Blood, 2017, 129(9): pp. 1103-1112.
Wikipedia, Peripheral T-cell lymphoma not otherwise specified, 4 pages.

ORGANOARSENIC COMPOUNDS AND METHODS FOR THE TREATMENT OF CANCER

CROSS-REFERENCE TO RELATED PATENT APPLICATIONS

This application is a U.S. Continuation of application Ser. No. 14/524,586, filed Oct. 27, 2014, which is a Continuation of application Ser. No. 13/059,176, filed Apr. 29, 2011 now abandoned, which is a U.S. National Phase Application under 35 U.S.C. § 371 of International Patent Application No. PCT/US2009/053858, filed Aug. 14, 2009 and claims the benefit of priority under 35 U.S.C. Section 119(e) of U.S. Application No. 61/189,511, filed Aug. 20, 2008, all of which are incorporated by reference in their entireties.

FIELD OF THE INVENTION

The present invention relates generally to the field of anti-cancer therapy. More particularly, it provides organic arsenic compounds and methods for their use in treating cancers such as leukemia and solid tumors.

BACKGROUND OF THE INVENTION

Despite progress in leukemia therapy, most adult patients with leukemia still die from disease progression. Arsenic trioxide, an inorganic compound, has been approved for the treatment of patients with relapsed or refractory acute promyelocytic leukemia (APL) and is being evaluated as therapy for other leukemia types. Preliminary data from China and the recent experience in the U.S., however, suggest a role for arsenic trioxide in the other hematologic cancers as well. Consequently, the activity of arsenic trioxide as an anti-leukemic agent is currently being investigated in many types of leukemia. Although the results look favorable in terms of the response rate of some of the leukemia types that are being investigated, systemic toxicity of arsenic trioxide is a problem (Soignet et al., 1999; Wiernik et al., 1999; Geissler et al., 1999; Rousselot et al., 1999).

The only organic arsenical (OA) manufactured for human use, melarsoprol, has been evaluated for antileukemic activity (WO9924029, EP1002537). Unfortunately, this compound is excessively toxic to patients with leukemia at concentrations used for the treatment of trypanosomiasis. Therefore, there is a need to identify arsenic derivatives that can be used for the treatment of hematologic malignancies and cancer in general, that have similar or greater activity and lower toxicity than arsenic trioxide.

SUMMARY OF THE INVENTION

The present invention provides organic arsenical compounds with anti-cancer properties. In some embodiments, the present invention provides compounds having a structure of formula (I) or a pharmaceutically acceptable salt thereof

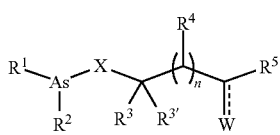
(I)

wherein
X is S or Se;
W is O, S, or (R)(R), where each occurrence of R is independently H or $C_{1-2}$alkyl;
n is an integer from 0 to 20;
$R^1$ and $R^2$ are independently $C_{1-30}$alkyl;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)$C_{1-10}$aralkyl, —OC(O)$C_{1-10}$alkyl, —OC(O)aryl, or a glutamine substituent;
$R^5$ is —OH, cyano, $C_{1-10}$alkoxy, amino, O-aralkyl, —OC(O)$C_{1-10}$aralkyl, —OC(O)$C_{1-10}$alkyl, —OC(O)aryl, or a glycine substituent; and
$R^6$ is H or $C_{1-10}$alkyl.

In certain embodiments, the organic arsenicals are compounds having a structure of formula (II)

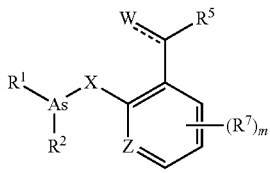
(II)

wherein
X is S or Se, preferably S;
W is O, S, or (R)(R), where each occurrence of R is independently H or a $C_{1-2}$alkyl, preferably O;
Z is CH or N, preferably N;
$R^1$ and $R^2$ are independently $C_{1-10}$alkyl, preferably $R^1$ and $R^2$ are independently selected from methyl, ethyl, propyl, and isopropyl; and
$R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;
$R^6$ is H or $C_{1-10}$alkyl;
$R^7$ is selected from halogen, —OH, $C_{0-6}$alkyl-COOR$^6$, $C_{1-6}$alkyl, $C_{1-6}$alkoxy, amino, amido, cyano, and nitro;
m is an integer from 0 to 4, preferably 0.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a number of organic arsenic compounds.

In certain embodiments, the organic arsenicals of the present invention have a structure of formula (I) or a pharmaceutically acceptable salt thereof

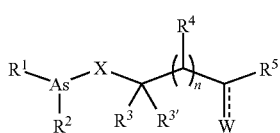

(I)

wherein

X is S or Se, preferably S;

W is O, S, or (R)(R), where each occurrence of R is independently H or a $C_{1-2}$alkyl, preferably O or (R)(R);

n is an integer from 0 to 20;

$R^1$ and $R^2$ are independently $C_{1-30}$alkyl;

$R^3$ is —H, $C_{1-10}$alkyl, or $C_{0-6}$alkyl-COOR$^6$;

$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;

$R^4$ is —OH, —H, —CH$_3$, amino, —OC(O)C$_{1-10}$aralkyl, —OC(O)C$_{1-10}$alkyl, —OC(O)aryl, or a glutamine substituent;

$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and $R^6$ is H or $C_{1-10}$alkyl, preferably H.

In certain embodiments, W is (R)(R) and each occurrence of R is independently H or a $C_{1-2}$alkyl. In certain such embodiments, each occurrence of R is H.

In certain embodiments, n is 0 or 1, preferably 1. In certain embodiments, n is an integer from 2 to 20, preferably from 5 to 20 or 9 to 14.

In certain embodiments, $R^1$ and $R^2$ are each independently $C_{11-30}$alkyl, preferably $C_{12-28}$alkyl, $C_{13-25}$alkyl, $C_{14-22}$alkyl, or even $C_{15-20}$alkyl.

In certain embodiments, $R^1$ and $R^2$ are $C_{1-10}$alkyl, preferably $R^1$ and $R^2$ are independently selected from methyl, ethyl, propyl, and isopropyl In certain embodiments, $R^3$ is —H or $C_{0-6}$alkyl-COOR$^6$. In certain such embodiments, $R^3$ is selected from —COOR$^6$, —CH$_2$COOR$^6$, —CH$_2$CH$_2$COOR$^6$, —CH(CH$_3$)COOR$^6$, —CH(CH$_2$CH$_3$)COOR$^6$, or —CH$_2$CH$_2$CH$_2$COOR$^6$, wherein $R^6$ is $C_{1-10}$alkyl.

In certain embodiments, $R^3$ is $C_{1-10}$alkyl. In certain preferred such embodiments, $R^3$ is selected from methyl, ethyl, propyl, and isopropyl, preferably methyl.

In certain embodiments, $R^{3'}$ is selected from amino, cyano, halogen, aryl, aralkyl, heteroaryl, heteroaralkyl, carboxyl, $C_{1-10}$alkyl, $C_{1-10}$alkenyl, and $C_{1-10}$alkynyl. In preferred such embodiments, $R^{3'}$ is selected from aryl, aralkyl, heteroaryl, heteroaralkyl, carboxyl, $C_{1-10}$alkenyl, and $C_{1-10}$alkynyl In certain embodiments, $R^4$ is selected from —OH, —H, —CH$_3$, —OC(O)C$_{1-10}$aralkyl, —OC(O)C$_{1-10}$alkyl, and —OC(O)aryl. In certain such embodiments, $R^4$ is selected from —OC(O)C$_{1-10}$aralkyl, —OC(O)C$_{1-10}$alkyl, and —OC(O)aryl.

In certain embodiments, $R^4$ is amino. In certain such embodiments, $R^4$ is NH$_2$.

In certain embodiments, $R^4$ is a glutamine substituent.

In certain embodiments, $R^5$ is selected from cyano, $C_{1-10}$alkoxy, amino, O-aralkyl, —OC(O)C$_{1-10}$aralkyl, —OC(O)C$_{1-10}$alkyl, and —OC(O)aryl.

In certain embodiments, X is S, W is (R)(R), wherein each occurrence of R is H, n is 1, $R^1$ and $R^2$ are independently selected from methyl, ethyl, propyl, and isopropyl, $R^3$ and $R^{3'}$ are H, $R^4$ is selected from OH, —OC(O)C$_{1-10}$aralkyl, —OC(O)C$_{1-10}$alkyl, and —OC(O)aryl and, and $R^5$ is selected from OH, —OC(O)C$_{1-10}$aralkyl, —OC(O)C$_{1-10}$alkyl, and —OC(O)aryl. In certain such embodiments, $R^1$ and $R^2$ are the same and are together selected from methyl, ethyl, propyl, and isopropyl.

In certain embodiments, X is S, W is O, n is 1, $R^1$ and $R^2$ are both methyl, $R^3$ is selected from H and COOR$^6$, $R^{3'}$ is H, and $R^4$ is selected from H and a glutamine substituent, and $R^5$ is selected from OH and a glycine substituent. In certain such embodiments, $R^3$ is COOR$^6$, $R^4$ is H, $R^5$ is OH, and $R^6$ is H.

In certain embodiments, compounds of formula (I) are selected from

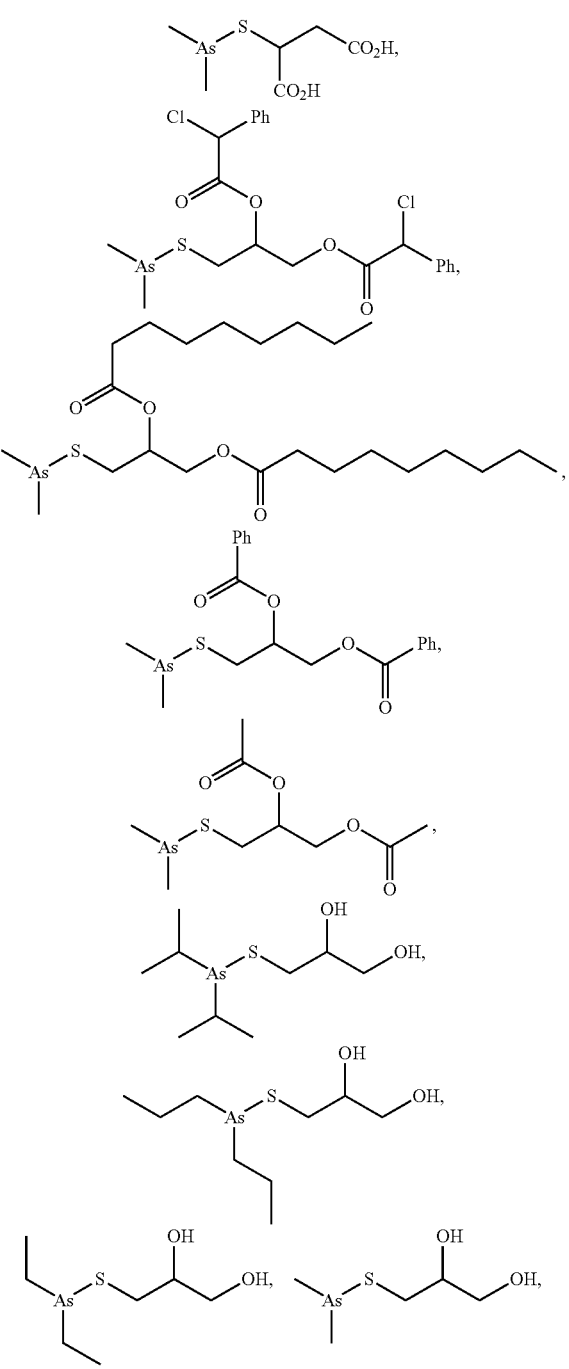

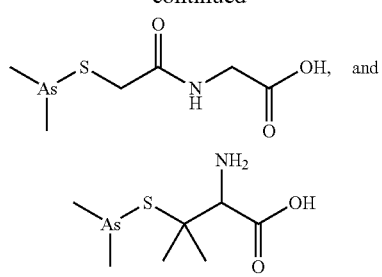

or a pharmaceutically acceptable salt thereof.

In certain embodiments, compounds of formula (I) are selected from

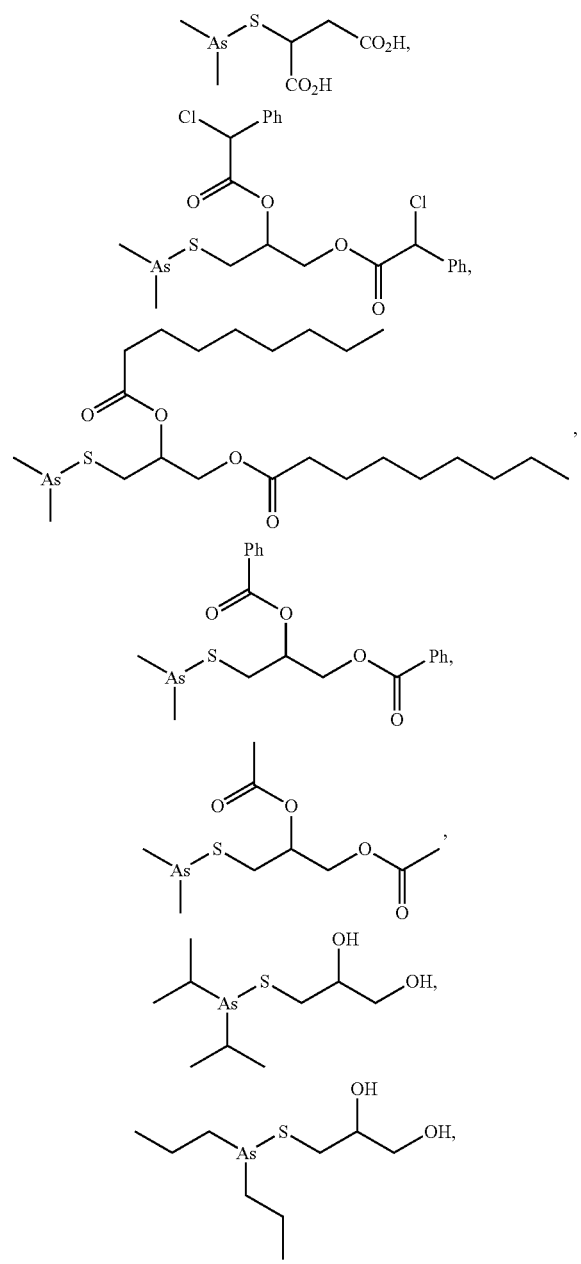

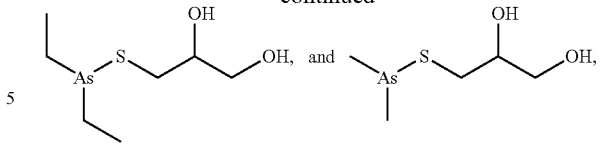

or a pharmaceutically acceptable salt thereof.

In certain embodiments, compounds of formula (I) are selected from

or a pharmaceutically acceptable salt thereof.

In certain embodiments, compounds of formula (I) are selected from

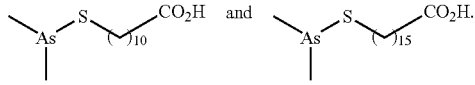

In certain embodiments, a compound of formula (I) is

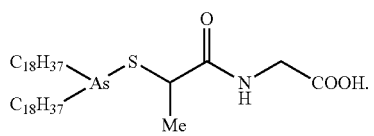

In certain embodiments, a compound of formula (I) is

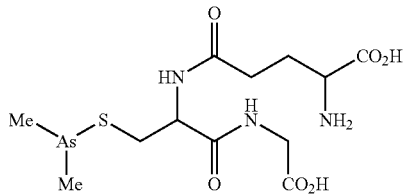

or a pharmaceutically acceptable salt thereof.

If a chiral center is present, all isomeric forms are within the scope of the invention. Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5-6, pp 177-178, which section is hereby incorporated by reference.

In certain embodiments, the organic arsenicals are compounds having a structure of formula (II)

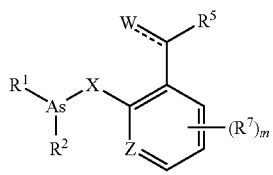

(II)

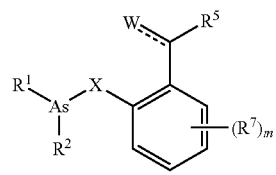

(III)

wherein

X is S or Se, preferably S;

W is O, S, or (R)(R), where each occurrence of R is independently H or a $C_{1-2}$alkyl, preferably O;

Z is CH or N;

$R^1$ and $R^2$ are independently $C_{1-10}$alkyl, preferably $R^1$ and $R^2$ are independently selected from methyl, ethyl, propyl, and isopropyl; and $R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;

$R^6$ is H or $C_{1-10}$alkyl;

$R^7$ is selected from halogen, —OH, $C_{0-6}$alkyl-COOR$^6$, $C_{1-6}$alkyl, $C_{1-6}$alkoxy, amino, amido, cyano, and nitro;

m is an integer from 0 to 4, preferably 0.

In certain embodiments, W is (R)(R) and each occurrence of R is independently H or a $C_{1-2}$alkyl. In certain such embodiments, each occurrence of R is H.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments X is S, W is O, $R^1$ and $R^2$ are independently selected from methyl, ethyl, propyl, and isopropyl, and $R^5$ is OH. In certain such embodiments, $R^1$ and $R^2$ are the same and are together selected from methyl, ethyl, propyl, and isopropyl. In certain such embodiments, $R^1$ and $R^2$ are both methyl.

In certain embodiments, Z is N.

In certain embodiments, Z is CH.

In certain embodiments, a compound of formula (II) is selected from

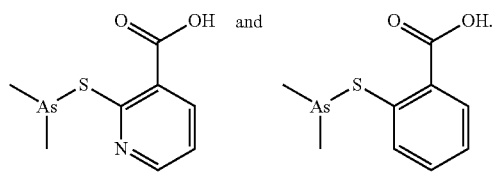

In certain embodiments, a compound of formula (II) is

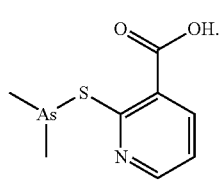

In other embodiments, the organic arsenicals are compounds having a structure of formula (III)

wherein

X is S or Se, preferably S;

W is O, S, or (R)(R), where each occurrence of R is independently H or a $C_{1-2}$alkyl, preferably O;

$R^1$ and $R^2$ are independently $C_{1-10}$alkyl, preferably $R^1$ and $R^2$ are independently selected from methyl, ethyl, propyl, and isopropyl; and $R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;

$R^6$ is H or $C_{1-10}$alkyl;

$R^7$ is selected from halogen, —OH, $C_{0-6}$alkyl-COOR$^6$, $C_{1-6}$alkyl, $C_{1-6}$alkoxy, amino, amido, cyano, and nitro;

m is an integer from 0 to 4, preferably 0.

In certain embodiments, W is (R)(R) and each occurrence of R is independently H or a $C_{1-2}$alkyl. In certain such embodiments, each occurrence of R is H.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments X is S, W is O, $R^1$ and $R^2$ are independently selected from methyl, ethyl, propyl, and isopropyl, and $R^5$ is OH. In certain such embodiments, $R^1$ and $R^2$ are the same and are together selected from methyl, ethyl, propyl, and isopropyl. In certain such embodiments, $R^1$ and $R^2$ are both methyl.

In certain preferred embodiments, a compound of formula (II) has the following structure

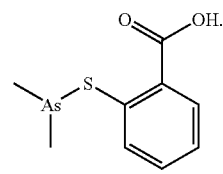

The invention further provides pharmaceutical compositions comprising formula (I), formula (II), or formula (III), or a pharmaceutically acceptable salt thereof, and a pharmaceutically acceptable diluent or carrier. In certain embodiments, the pharmaceutical composition is an aqueous solution that has a pH greater than about 5, preferably in the range from about 5 to about 8, more preferably in the range from about 5 to about 7.

Another aspect of the invention provides a method for the treatment of cancer comprising administering a therapeutically effective amount of a compound of formula (I), formula (II), or formula (III).

The invention also relates to the use of a compound of formula (I), formula (II), or formula (III), or a pharmaceutically acceptable salt thereof, in the manufacture of a medicament for the treatment of cancer.

In certain embodiments, the cancer is selected from a solid tumor, such as brain, lung, liver, spleen, kidney, lymph node, small intestine, pancreas, blood cells, bone, colon, stomach, breast, endometrium, prostate, testicle, ovary, central nervous system, skin, head and neck, esophagus, or bone marrow, or a hematological cancer, such as leukemia, acute promyelocytic leukemia, lymphoma, multiple myeloma, myelodysplasia, myeloproliferative disease, or refractory leukemia. In certain such embodiments, the cancer is a leukemia selected from acute and chronic leukemia.

In certain embodiments, the cancer is a lymphoma selected from non-Hodgkin's and Hodgkin's lymphoma. In certain embodiments, the non-Hodgkin's lymphoma is selected from peripheral T-cell lymphoma (PTCL), diffuse large B-cell lymphoma, and marginal zone lymphoma. In certain embodiments, the Hodgkin's lymphoma is Hodgkin's nodular sclerosis.

Thus, in another aspect, the invention comprises a method of treating a patient with cancer comprising administering to the patient a composition comprising a compound of formula I, formula TI, or formula III, or pharmaceutical composition as described above. The therapeutically effective amount of a compound may be 0.1-1000 mg/kg, 1-500 mg/kg, or 10-100 mg/kg. In particular embodiments, the method may comprise administering the composition daily. It is further contemplated that treatment methods may involve multiple administrations. The method may comprise administering the compound daily such as by injection. Alternative routes and methods of administration described in the specification may also be used and the mode of administration will mainly depend on the type and location of the cancer. In certain embodiments, the method further comprises administering one or more additional agents to the patient. The additional agent may be all-trans-retinoic acid, 9-cis retinoic acid, Am-80, or ascorbic acid. The use of other adjunct cancer therapies, such as chemotherapy, radiotherapy, gene therapy, hormone therapy, and other cancer therapies known in the art are also contemplated in conjunction with the methods of the present invention.

Various methods of administration are contemplated, including regional, systemic, direct administration and by perfusion. Such methods include administration by injection, oral routes, intravenous, intraarterial, intratumoral, administration to tumoral vasculature, intraperitoneal, intratracheal, intramuscular, endoscopical, intralesional, percutaneous, subcutaneous, topical, nasal, buccal, mucosal, anogenital, rectal and the like.

Definitions

The term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "$C_{1\text{-}6}$alkoxy" refers to an $C_{1\text{-}6}$alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1\text{-}6}$aralkyl", as used herein, refers to a $C_{1\text{-}6}$alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "regimen" is a predetermined schedule of one or more therapeutic agents for the treatment of a cancer. Accordingly, when a therapeutic agent is administered "alone," the regimen does not include the use of another therapeutic agent for the treatment of cancer.

In certain embodiments, the compound is administered daily for five days every four weeks. In certain embodiments, the compound is administered once daily for five days every four weeks, preferably for five consecutive days. In certain alternative embodiments, the compound is administered two days a week for three weeks, followed by one week off. In certain such embodiments, the compound is administered for two consecutive days or two non-consecutive days (e.g., with one, two, three, or even four days in between doses) a week for three weeks, followed by one week off. In certain embodiments, these protocols can be repeated indefinitely.

In certain embodiments, such dosing is by intravenous administration. In certain alternative embodiments, such dosing is by oral administration. In certain such embodiments, the compound is administered intravenously at a dose of about 200-420 mg/m$^2$ or about 250 to 350 m/m$^2$. In certain embodiments, the compound is administered at a dose of about 200, about 250, about 300, about 350, about 400 or even about 420 mg/m$^2$. In certain embodiments, the compound is administered orally at a total daily dose of 300 to about 700 mg or about 400 to about 600 mg. In certain embodiments, the compound is administered at a total daily dose of 300, about 400, about 500, about 600, or even about 700 mg.

As used herein, the term "treating" or "treatment" includes reversing, reducing, or arresting the symptoms, clinical signs, and underlying pathology of a condition in manner to improve or stabilize a subject's condition.

Toxicity of Inorganic Vs. Organic Arsenicals

The use of arsenic trioxide is limited by its toxicity. OA, on the other hand, are much less toxic, to the extent that the methylation of inorganic arsenic in vivo into OA has been considered to be a detoxification reaction. The OA monomethylarsinic acid and dimethylarsinic acid are the primary metabolites of inorganic arsenic (Hughes et al., 1998). Inorganic arsenicals, including arsenic trioxide, have varied effects on many organ systems, including cardiovascular system, gastrointestinal tract, kidneys, skin, nervous system, and blood. Inorganic arsenicals are particularly toxic to the liver, causing infiltration, central necrosis, and cirrhosis (IARC, 1980: ACGIH, 1991; Beliles et al., 1994; Goyer et al., 1996). There is now sufficient evidence that inorganic arsenic compounds are skin and lung carcinogens in humans (Goyer et al., 1996).

The toxicity of a given arsenical is related to the rate of its clearance from the body and to the extent of its tissue accumulation (Beliles et al., 1994). In general, toxicity increases in the following sequence: organic arsenicals<$As^{5+}$<$As^{3+}$ (including arsenic trioxide)<arsine. Unlike inorganic arsenicals, no deaths or serious cases of toxicity due to OA have been reported in the literature. Consequently, in mammals the methylation of inorganic arsenic has been considered a detoxification mechanism because of the lower toxicity of methylated OA, and their fast excretion and low retention (Beliles et al., 1994; Goyer et al., 1996). A good example is that of dimethylarsinic acid, an organic compound, the predominant urinary metabolite excreted by most mammals after exposure to inorganic arsenic, including arsenic trioxide. In in vivo toxicity studies in mice, after intraperitoneal administration of arsenic trioxide, the $LD_{50}$ (a dose at which 50% of animals die due to acute toxicity) was 10 mg/kg, (Investigator's Brochure, 1998), while after administration of dimethylarsinic acid, the $LD_{50}$ was 500 mg/kg (MSDS, 1998).

Cancer Treatment

The organic arsenicals of the current invention may be used to treat a variety of cancers, including all solid tumors and all hematological cancers, including leukemia, lymphoma, multiple myeloma, myelodysplasia, or myeloproliferative disorders. The organic arsenical can also be used to treat hematological cancers that have become refractory to other forms of treatment.

In certain embodiments, the cancer is a lymphoma selected from non-Hodgkin's and Hodgkin's lymphoma. In certain embodiments, the non-Hodgkin's lymphoma is selected from peripheral T-cell lymphoma (PTCL), diffuse large B-cell lymphoma, and marginal zone lymphoma. In certain embodiments, the Hodgkin's lymphoma is Hodgkin's nodular sclerosis.

Lymphoma is a type of blood cancer that occurs when lymphocytes—white blood cells that help protect the body from infection and disease—begin behaving abnormally. Abnormal lymphocytes may divide faster than normal cells or they may live longer than they are supposed to. Lymphoma may develop in many parts of the body, including the lymph nodes, spleen, bone marrow, blood, or other organs. There are two main types of lymphomas: Hodgkin lymphoma and non-Hodgkin lymphoma (NHL).

Peripheral T-cell lymphomas are tumors composed of mature T-cells (not B-cells). Peripheral T-cell lymphomas such as angioimmunoblastic T-cell lymphoma or anaplastic large cell lymphoma can arise in lymph nodes, while others like subcutaneous panniculitis-like T-cell lymphoma, nasal NK/T-cell lymphoma, or intestinal T-cell lymphoma can arise in extranodal sites.

Large cell lymphomas are the most common type of lymphoma. These cancers may arise in lymph nodes or in extranodal sites, including the gastrointestinal tract, testes, thyroid, skin, breast, central nervous system, or bone and may be localized or generalized (spread throughout the body).

Marginal zone tumors are indolent B-cell lymphomas and may occur either outside lymph nodes (extranodal) or within lymph nodes (nodal). They are divided into two categories depending on the location of the lymphoma. Mucosa-associated lymphoid tissue lymphomas (also called MALT or MALTomas) are forms of marginal zone lymphomas that affect places outside the lymph nodes (such as the gastrointestinal tract, eyes, thyroid, salivary glands, lungs, or skin). Nodal marginal zone B-cell lymphomas are uncommon and are sometimes called monocytoid B-cell lymphomas.

In Hodgkin's nodular sclerosis, the involved lymph nodes contain areas composed of Reed-Sternberg cells mixed with normal white blood cells. The lymph nodes often contain prominent scar tissue, hence the name nodular sclerosis (scarring). This subtype is the most common, making up 60% to 75% of all cases of Hodgkin's lymphoma.

Pharmaceutical Compositions

The preparation of a pharmaceutical composition that contains at least one organic arsenical or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof; as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The organic arsenical may be combined with different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an organic arsenical compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The organic arsenical may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. Thus, preferred compositions have a pH greater than about 5, preferably from about 5 to about 8, more preferably from about 5 to about 7. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Combination Therapy

It is an aspect of this invention that the organic arsenical can be used in combination with another agent or therapy method, preferably another cancer treatment. The organic arsenical may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the organic arsenical. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the organic arsenical. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the organic arsenical is "A" and the secondary agent, which can be any other therapeutic agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery. The section below describes some adjunct cancer therapies:

Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and U V-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art will, in light of the present disclosure, appreciate that many changes can be made in the specific embodiments which are disclosed and still obtain a like or similar result without departing from the spirit and scope of the invention.

Example 1

Synthesis of S-Dimethylarsino-Thiosuccinic Acid (MER1), S-Dimethylarsino-Salicylic Acid (SAL1), and S-(Dimethylarsino) Glutathione (SGLU1)

MER-1: Mercaptosuccinic acid, 4.5 g, was placed in 100 mL of glyme (1,2-dimethoxyethane) in a 250 mL round-bottom flask. Four mL of dimethylchloroarsine (0.03 mol) was added drop-wise, followed by 4 mL of diethylamine (0.04 mol), again dropwise. The reaction mixture was stirred for 20 h at room temperature. A white precipitate of diethylamine hydrochloride was formed and was separated by filtration. The solution of MER1 in the glyme was greatly reduced in volume by evaporation at reduced pressure. White crystals of MER1 were separated by filtration and washed with cold distilled water. The colorless crystalline product was then recrystallized from ethanol-water to a constant melting point of 150° C.

SAL-1: In a 100 mL flask 5 g of 2-mercapto benzoic acid (thiosalicylic acid), 75 mL of glyme, 5 mL of dimethylchloroarsine, and 5 mL diethylamine were placed. The mixture was refluxed for 1 hour under an atmosphere of nitrogen and stirred at room temperature overnight. The precipitate of diethylamine hydrochloride was separated by filtration. The filtrate was evaporated slowly under reduced pressure until crystals of the product separate. The evaporated solution containing the product was chilled in ice and the cold solution was filtered. Crystals of the product were recrystallized from ethanol to a constant melting point of 97° C.

SGLU-1: Glutathione (14.0 g, 45.6 mmol) was stirred rapidly in glyme while dimethylchoroarsine (6.5 g, 45.6 mmol) was added dropwise. Pyridine (6.9 g, 91.2 mmol) was then added to the slurry and the mixture was subsequently heated to reflux. The heat was removed immediately and the mixture stirred at room temperature for 4 h. Isolation of the resultant insoluble solid and recrystallization from ethanol afforded 4 as the pyridine hydrochloride complex (75% yield): mp 115-118° C.; NMR (D$_2$O) δ1.35 (s, 6H), 1.9-4.1 (m's, 10H), 7.8-9.0 (m, 5H); mass spectrum (m/e) 140, 125, 110, 105, 79, 52, 45, 36. This material is not used for the examples described herein, but has been used in biological assays as described in Banks, C. H., et al. (J. Med. Chem. (1979) 22: 572-575), which is incorporated herein by reference in its entirety.

Example 2

Alternate Synthesis of S-Dimethylarsinoglutathione

The following procedure describes the manner of preparation of S-dimethylarsinoglutathione. The quantities used can be multiplied or divided with equal success if the respective ratios are maintained.

Dimethylchloroarsine.

Dimethylarsinic acid, (CH$_3$)$_2$As(O)OH was supplied by the Luxembourg Chemical Co., Tel Aviv, Israel. The product was accompanied by a statement of its purity and was supplied as 99.7% pure. The dimethylarsinic acid was dissolved in water-hydrochloric acid to pH 3. A stream of sulfur dioxide was passed through this solution for about one hour. Dimethylchloroarsine separated as a heavy, colorless oil. The two liquid phases, water/(CH$_3$)$_2$AsCl were separated using a separatory funnel. The chlorodimethylarsine was extracted into diethylether and the ether solution was dried over anhydrous sodium sulfate. The dried solution was transferred to a distillation flask which was heated slowly to evaporate the ether. The remaining liquid, dimethylchloroarsine was purified by distillation. The fraction boiling at 106-109° C. was collected. The product, a colorless oil, displays a simple $^1$H NMR resonance at 1.65 ppm.

S-Dimethylarsinoglutathione

In a 500 mL flask, 7 g of glutathione was used as received from the Aldrich Chemical Co., purity 98% and dissolved in 250 mL of 1,2-dimethoxyethane. To this solution was added 3.3 g of dimethylchloroarsine. This was followed by the addition of 3.5 g of pyridine (redistilled after drying over NaOH pellets). The solution was refluxed for one hour after which time it was stirred at room temperature for three hours.

The desired product, S-dimethylarsinoglutathione was separated as the pyridine hydrochloride complex. The solid was removed by filtration and washed thoroughly with 1,2-dimethoxyethane. It was subsequently dried over anhydrous calcium chloride in vacuo. The yield of S-dimethylarsinoglutathione pyridine hydrochloride was 10.3 g and the melting point was 135-140° C. This material was used in the biological assays described above in examples 2 to 12.

Example 3

Pyridine Hydrochloride Free Synthesis of S-dimethylarsinoglutathione (GLU)

Dimethylarsinoglutathione is made using an adapted of Chen (Chen, G. C., et al. Carbohydrate Res. (1976) 50: 53-62) the contents of which are hereby incorporated by reference in their entirety. Briefly, dithiobis(dimethylarsinoglutamine) is dissolved in dichloromethane under nitrogen. Tetramethyldiarsine is added dropwise to the solution and the reaction is stirred overnight at room temperature under nitrogen and then exposed to air for 1 h. The mixture is then evaporated to dryness and the residue is washed with water and dried to give a crude solid that is recrystallized from methanol to give S-dimethylarsinoglutathione.

Example 4

Third Synthesis of Pyridine Hydrochloride Free 5-Dimethylarsinoglutathione (GLU)

S-dimethylarsinoglutathione is made using the procedure of Cullen et al. (J. Inorg. Biochem. (1984) 21: 179-194) the contents of which are hereby incorporated by reference in their entirety. Briefly, dimethylarsinic acid and glutathione are dissolved in water under a nitrogen atmosphere and stirred. The resulting solution is stirred for 12 h and then evaporated to dryness under reduced pressure without heating to give a solid that is extracted with cold methanol. The methanol solution is then evaporated to dryness under reduced pressure and the resulting solid is recrystallized from methanol/water, collected, and dried to give S-dimethylarsinoglutathione.

Example 5

Preparation of Dimethylchloroarsine

A 3 L, 3 necked round bottom flask was equipped with a mechanical stirrer assembly, an additional funnel, thermometer, nitrogen inlet, and a drying tube was placed in a bath. The flask was charged with cacodylic acid (250 g) and concentrated HCl (825 mL) and stirred to dissolve. After the cacodylic acid was completely dissolved, the solution was warmed to 40° C. To the stirring solution, hypophosphorous acid ($H_3PO_2$) (50% solution, 250 g) was added dropwise, maintaining the reaction temperature between 40-50° C. After approximately 50 mL of $H_3PO_2$ had been added, the solution became cloudy and the temperature of the reaction rose rapidly at which time an external cooling bath was used to maintain the reaction temperature between 40-50° C. The addition of the $H_3PO_2$ was continued, maintaining the reaction temperature in the desired range. After the addition of $H_3PO_2$ was complete, the reaction was held between 40-45° C. for 15 minutes while stirring. The external bath was removed and the stirring was continued. The reaction was allowed to stir and cool to <30° C. After the temperature of the reaction mixture dropped to 30° C. or less, methylene chloride (300 mL) was added and the resulting mixture was stirred to extract the product into the methylene chloride. Stirring was discontinued and the layers were allowed to separate over ½ hour. The layers were separated and the methylene chloride layer was dried over anhydrous sodium sulfate with stirring for a minimum of 1 hour. The mixture may be allowed to sit under a nitrogen atmosphere for a maximum of 72 hours. The organic mixture was filtered to remove the sodium sulfate and the methylene chloride was removed by atmospheric distillation. The crude residual product was distilled under a nitrogen atmosphere, through an 8" Vigreux or packed column. The product fraction with bp 104-106° C. at atmospheric pressure was collected.

Preparation of S-Dimethylarsinoglutathione

A 5 L, three necked round bottom flask was equipped with a mechanical stirrer assembly, thermometer, addition funnel, nitrogen inlet, and a drying tube was placed in a cooling bath. A polyethylene crock was charged with glutathione-reduced (200 g) and deionized water (2 L) and stirred under a nitrogen atmosphere to dissolve all solids. The mixture was filtered to remove any insoluble material and the filtrate was transferred to the 5 L flask. While stirring, ethanol, 200 proof (2 L) was added and the clear solution was cooled to 0-5° C. using an ice/methanol bath. Pyridine (120 g) was added followed by a dropwise addition of $Me_2AsCl$ (120 g) over a minimum of 1 hour. The reaction mixture was stirred at 0-5° C. for a minimum of 2 hours prior to removal of the cooling bath and allowing the mixture to warm to room temperature under a nitrogen atmosphere with stirring. The reaction mixture was stirred overnight (>15 hrs) at room temperature under a nitrogen atmosphere at which time a white solid may precipitate. The reaction mixture was concentrated to a slurry (liquid and solid) at 35-45° C. using oil pump vacuum to provide a white solid residue. As much water as possible is removed, followed by two coevaporations with ethanol to azeotrope the last traces of water. The white solid residue was slurried in ethanol, 200 pf. (5 L) under a nitrogen atmosphere at room temperature overnight. The white solid was filtered and washed with ethanol, 200 pf. (2×500 mL) followed by acetone, ACS (2×500 mL). The resulting solid was transferred to drying trays and vacuum oven dried overnight at 25-35° C. using oil pump vacuum to provide pyridinium hydrochloride-free S-dimethylarsinoglutathione as a white solid with a melting point of 189-190° C.

Preparation of Dosage Form of S-Dimethylarsinoglutathione

A solution of S-dimethylarsinoglutathione in water for injection (WFI) was adjusted to pH 5.0 to 5.5 with NaOH or HCl. The resulting solution was then filtered through a 0.2 micron Sartopore 2 filter and a Flexicon filling unit was used to deliver 150 mg per Type 1 borosilicate glass vial (Wheaton). The filled vials were then lyophilized in a Hull 48 Lyophilizer unit by first loading the vials on the shelf and ramping the temperature to −40° C. at a cooling rate of 0.5° C. per minute. The shelf temperature was then held at −40° C. for 300 minutes. A vacuum was then applied at 75 micron and the shelf temperature was ramped up to 5° C. at a rate of 0.1° C. per minute. The shelf temperature was then held at 5° C. for 1,000 minutes before applying the vacuum at 50 micron. The shelf temperature was then ramped up to 25° C. at a rate of 0.1° C. per minute and the temperature was held at 25° C. for 720 minutes. The shelf temperature was then reduced to 5° C. and held until the final stoppering step, at which time the chamber was returned to 640,000 mm Torr with nitrogen and the vials were stoppered with gray butyl lyophilization stoppers and finally crimped with aluminum seals to provide S-dimethylarsinoglutathione as a white to off-white cake with a moisture content of 1.8%. The total time for the lyophilization procedure was 47 hours. The lyophilized S-dimethylarsinoglutathione was then reconstituted with 2.0 mL sterile water to provide a clear, colorless solution with a final concentration of 75±7.5 mg S-dimethylarsinoglutathione per mL and a pH of 4.5 to 6.0.

Example 6

Preparation of Dimethylchloroarsine (DMCA)

A 3-neck round-bottom flask (500 mL) equipped with mechanical stirrer, inlet for nitrogen, thermometer, and an ice bath was charged with cacodylic acid (33 g, 0.23 mol) and conc. hydrochloric acid (67 mL). In a separate flask, a solution of $SnCl_2.2H_2O$ (54 g, 0.239 mol) in conc. hydrochloric acid (10 mL) was prepared. The $SnCl_2.2H_2O$ solution was added to the cacodylic acid in HCl solution under nitrogen while maintaining the temperature between 5° C. and 10° C. After the addition was complete, the ice bath was removed and the reaction mixture was stirred at ambient temperature for 1 h. The reaction mixture was transferred to a separatory funnel and the upper layer (organic) collected. The bottom layer was extracted with dichloromethane (DCM) (2×25 mL). The combined organic extract was washed with 1 N HCl (2×10 mL) and water (2×20 mL). The organic extract was dried over $MgSO_4$ and DCM was removed by rotary evaporation (bath temperature 80° C., under nitrogen, atmospheric pressure). The residue was further distilled under nitrogen. Two fractions of DMCA were collected. The first fraction contained some DCM and the second fraction was of suitable quality (8.5 g, 26% yield). The GC analysis confirmed the identity and purity of the product.

Preparation of S-Dimethylarsinoglutathione (SGLU-1)

A suspension of glutathione (18 g, 59 mmol) in a mixture of water/ethanol 1:1 v/v (180 mL) was cooled below 5° C. and under an inert atmosphere treated with triethylamine (10 mL, 74 mmol) in one portion. The mixture was cooled to 0-5° C. and DMCA (11 g, 78.6 mmol) was added dropwise over a period of 10 min, while maintaining the temperature below 5° C. The reaction mixture was stirred at 0-5° C. for 4 h, and the resulting solids were isolated by filtration. The product was washed with ethanol (2×50 mL) and acetone (2×50 mL) and dried in vacuum at RT overnight, to give 11 g (46%) of SGLU-1. HPLC purity was 97.6% by area (average of 3 injections), Anal. Calcd. for $C_{12}H_{22}AsN_3O_6S$: C, 35.04; H, 5.39; N, 10.12, S, 7.8. Found: C, 34.92; H, 5.31; N, 10.27, S, 7.68. $^1H$ and $^{13}C$-NMR were consistent with the structure. The filtrate was diluted with acetone (150 mL) and placed in a refrigerator for 2 days. An additional 5.1 g (21%) of SGLU-1 was isolated as the second crop, HPLC purity was 97.7% by area (average of 3 injections).

Preparation of S-Dimethylarsinoglutathione (SGLU-1)

In a 3 L three-neck flask equipped with a mechanic stirrer, dropping funnel and thermometer under an inert atmosphere was prepared a suspension of glutathione (114.5 g, 0.37 mol) in a 1:1 (v/v) mixture of water/ethanol (1140 mL) and cooled to below 5° C. The mixture was treated slowly (over 15 min) with triethylamine (63.6 mL, 0.46 mol) while maintaining the temperature below 20° C. The mixture was cooled to 4° C. and stirred for 15 min and then the traces of undissolved material removed by filtration. The filtrate was transferred in a clean 3 L three-neck flask equipped with a mechanic stirrer, dropping funnel, nitrogen inlet, and thermometer and DMCA (70 g, 0.49 mol) (lot #543-07-01-44) was added slowly while maintaining the temperature at 3-4° C. The reaction mixture was stirred at 1-4° C. for 4 h, and acetone (1.2 L) was added over a period of 1 h. The mixture was stirred for 90 min between 2 and 3° C. and the resulting solid was isolated by filtration. The product was washed with ethanol (2×250 mL) and acetone (2×250 mL) and the wet solids were suspended in ethanol 200 Proof (2000 mL). The product was isolated by filtration, washed with ethanol (2×250 mL) and acetone (2×250 mL) and dried in vacuum for 2 days at RT to give 115 g (75%) of SGLU-1, HPLC purity>99.5% (in process testing).

Example 7

In Vitro Evaluation of Anti Cancer Activity of GMZ27

GMZ27, an organic arsine having the following structure

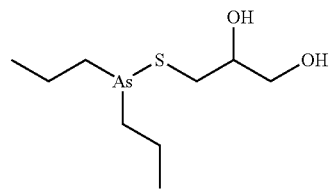

was tested in 72 hour MTS assays against different human acute myelocytic leukemia (AML) cell lines and it was found that the $IC_{50}$ was 0.56-0.86 μM. This activity was higher than the activity of arsenic trioxide against these cell lines (FIG. 27A). The anti-leukemic activity of GMZ27 was then evaluated in a long-term (7 day) colony-forming assay, where cells are grown in semi-solid medium. GMZ27 had significantly higher activity than arsenic trioxide against both human leukemia cell lines and leukemic cells obtained from patients with acute or chronic leukemia (FIG. 27B).

The mechanisms of anti-cancer activity of GMZ27 and arsenic trioxide were then compared. Arsenic trioxide (ATO) exerted its anti-leukemic activity in cells other than APL via several mechanisms, including induction of apoptosis, alteration in the production of intracellular ROS resulting in the modulation of cellular GSH redox system, cell differentiation/maturation and possible effect on cell cycle regulation.

GMZ27 was more potent in induction of apoptosis than ATO. Results show that it activated the mitochondrial apoptotic pathway, as it altered mitochondrial membrane potential and cleaved caspase 9, but also by alternate, extrinsic, pathway since it cleaved caspase 8. This resulted in the induction of caspase 3 activity, cleavage of PARP, and binding of annexin V to the cells (FIGS. 28 and 29).

Pretreatment of leukemic cells with buthionine sulfoximine (BSO) renders them more sensitive to GMZ27; while pretreatment with dthiothreitol (DTT) or N-acetylcysteine (NAC), which may increase intracellular GSH, rendered the cells less sensitive (FIG. 30). This suggested that GMZ27, like ATO, modulates the GSH redox system in leukemic cells, however, it did so earlier and to a greater extent than ATO did (FIG. 31).

GMZ27, at low doses, was found to partially induce cell differentiation/maturation as judged by the induction of CD11b maturation marker on the surface of cells. This effect was marginal compared with that of ATO (FIG. 32). GMZ27 had no effect on the cell cycle progression (FIG. 33).

Toxicity of GMZ7 against healthy donor peripheral blood mononuclear cells has been evaluated in a long-term colony forming assay. GMZ27 was less toxic to normal cells than ATO (FIG. 34).

Studies to determine the toxicity of a single dose injection of GMZ27 were performed in normal Swiss-Webster mice. Toxicity was measured on the basis of mortality. It was found that the concentration of GMZ27 that kills 50% of mice ($LD_{50}$) was 100 mg/kg. In contrast, the $LD_{50}$ for ATO was much lower, at only 10 mg/kg.

Example 8

Preparation of
N-(2-S-Dimethylarsinothiopropionyl)Glycine

N-(2-mercaptopropionyl)glycine (0.02 mol, 3.264 g) was placed in 1,2-dimethoxyethane (50 mL) and dimethylchloroarsine (0.025 mol, 3.52 g) was added dropwise. The reaction mixture was stirred for 4 h at room temperature. A white precipitate of triethylamine hydrochloride salt was then separated by filtration and the solubtion was reduced in volume by evaporation at reduced pressure. The resulting residue was purified by column chromatography to afford the desired product (3.5 g).

Example 9

Preparation of 2-(S-Dimethylarsino)Thionicotinic Acid

2-Mercaptonicotinic acid (0.02 mol, 3 g) was placed in dichloromethane (50 mL) and dimethylchloroarsine (0.025 mol, 3.52 g) was added dropwise. The reaction was stirred at reflux for 4 h. The dichloromethane was then removed by distillation and the residue was dissolved in diethyl ether (50 mL) and washed with water (3x). The solution was dried over $Na_2SO_4$, filtered, and the desired product was obtained as a pale yellow solid after concentration under reduced pressure.

Example 10

L-(+)-2-Amino-3-(Dimethylarsino)Thio-3-Methylbutanoic Acid

L-(+)-2-amino-3-mercapto-3-methylbutanoic acid (0.01 mol, 1.55 g) was placed in dichloromethane (50 mL) and dimthylchloroarsine (0.015 mol, 2.1 g) in dichlorormethane (5 mL) was added dropwise followed by the dropwise addition of triethylamine (1.6 g). The mixture was stirred for 4 h and the desired product appeared as a floating white crystalline solid after filtration of the reaction mixture. The crystalline solid was washed with dichloromethane, ethyl acetate, and acetone sequentially to provide the desired product (1.6 g; mp 107-109° C.).

Example 11

A Phase II multi-center trial of SGLU-1 (darinaparsin) was conducted in patients diagnosed with advanced lymphomas. Eligible patients required therapy and received at least 1 prior therapy. Patients received 300 mg/m² of darinaparsin intravenously for 5 consecutive days every 28 days (1 cycle) and were then evaluated for efficacy and safety by standard criteria. Treatment continued until toxicity or progression. To date the study has accrued 22 patients (15 non Hodgkin's [NHL], 7 Hodgkin's); 12 are male and 10 are female. Median age at baseline was 60.5 years (range: 28-80), ECOG performance status was <2, and median number of prior therapies was 3 (range: 1-6). Thirteen subjects have received at least 2 cycles of SGLU-1 and are evaluable for efficacy. Of these, 1 (diagnosed with peripheral T-cell lymphoma (PTCL)) has achieved a complete response (CR), 3 (diagnosed with diffuse large B-cell, marginal zone, and Hodgkin's nodular sclerosis, respectively) have achieved partial responses (PRs), and 2 patients with NHL have achieved stable disease (SD). In the patient with marginal zone lymphoma who achieved PR, no evidence for macroscopic disease was present, but microscopic disease was detectable on random biopsies from normal appearing gastric mucosa. All responders had been heavily pretreated (PTCL: CHOP (cyclophosphamide, doxorubicin, vincristine, and prednisolone)×6, ICE (ifosfamide, carboplatin and etoposide)×1, and EPOCH (etoposide, vincristine, doxorubicin, cyclophosphamide, and prednisone)×2; diffuse B-cell: RCHOP (rituximab, cyclophosphamide, doxorubicin, vincristine, and prednisolone)×5, RICE (rituximab, ifosfamide, carboplatin and etoposide)×3, and radiation therapy; marginal zone: rituximab×8, RCVP (rituximab, cyclophosphamide, vincristine and prednisolone)×1, and gemcitabine×1; and Hodgkin's: ICE×1, CBV (cyclophosphamide, carmustine and etoposide)×1, gemcitabine+MDX-060 (Medarex)×6). A total of 49 cycles of SGLU-1 have been administered. The only Grade 3 adverse event (AE) considered drug-related was wheezing. A total of 12 subjects have reported 37 serious adverse events (SAEs) while on study. Of these, only 2 had SAEs that were considered drug-related (neutropenic fever, fall). In conclusion, SLGU-1 has been very well tolerated and has demonstrated promising activity in heavily pretreated patients diagnosed with advanced lymphoma. Initial responses (1 CR, 3 PRs, 2 SDs) have been observed among 13 evaluable patients.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

All of the above-cited references and publications are hereby incorporated by reference.

The invention claimed is:
1. A method of treating a lymphoma selected from diffuse large B-cell lymphoma, marginal zone lymphoma, and Hodgkin's nodular sclerosis in a subject, the method comprising intravenously administering a compound of Formula (I) or a pharmaceutically acceptable salt thereof:

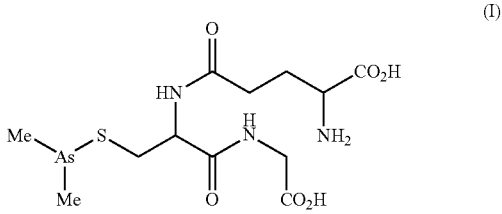

to thereby treat the subject, wherein a dose of the compound or a pharmaceutically acceptable salt thereof is 300 mg/m², and the compound or a pharmaceutically acceptable salt thereof is administered daily for 5 consecutive days every 3-4 weeks.

2. The method of claim 1, wherein the lymphoma comprises relapsed or refractory lymphoma.

* * * * *